(12) United States Patent
Ohm (10) Patent No.: US 7,865,314 B1
(45) Date of Patent: Jan. 4, 2011

(54) METHOD FOR DETERMINING THE SALT CONTENT OF LIQUID AND DEVICE FOR CARRYING OUT SAID METHOD

(75) Inventor: Klaus Ohm, Bremerhaven (DE)

(73) Assignee: Stiftung Alfred-Wegener-Institut Fuer Polar-Und Meeresforschung, Bremerhaven (DE)

( * ) Notice: Subject to any disclaimer, the term of this patent is extended or adjusted under 35 U.S.C. 154(b) by 0 days.

(21) Appl. No.: 10/009,971

(22) PCT Filed: Apr. 26, 2000

(86) PCT No.: PCT/DE00/01313

§ 371 (c)(1),
(2), (4) Date: Oct. 30, 2001

(87) PCT Pub. No.: WO00/67008

PCT Pub. Date: Nov. 9, 2000

(30) Foreign Application Priority Data

Apr. 30, 1999 (DE) ............... 199 21 079

(51) Int. Cl.
*G01N 31/00* (2006.01)
(52) U.S. Cl. ....................... 702/23
(58) Field of Classification Search ............ 702/23; 73/40, 5 R; 324/441, 639, 696, 448
See application file for complete search history.

(56) References Cited

U.S. PATENT DOCUMENTS 3,491,287 A * 1/1970 Brown .................. 324/445

(Continued)

FOREIGN PATENT DOCUMENTS

JP 04110760 4/1992

OTHER PUBLICATIONS

Bermuda biological station for research INC Bermuda atlantic time series study Chapter 5. Salinity determination, pp. 25-28.*

(Continued)

*Primary Examiner*—Aditya Bhat
(74) *Attorney, Agent, or Firm*—Leydig, Voit & Mayer, Ltd.

(57) ABSTRACT

Known methods use the temperature of the water bath which surrounds the liquid sample as the adjusting parameter. The aim in these methods is to maintain the water bath at a constant temperature in order to fulfill the prerequisites for calibration. In contrast, in the inventive method a measurement is determined for the maximum permissible drift ($\alpha_{max}$) in the temperature of the water bath ($\theta_B$) which is measured as the equivalent of the sample temperature ($\theta_P$). This greatly simplifies the problem of adjusting the temperature which primarily arises as a result of the delays in the control circuit. The adjusting element need only recognize a drift ($\alpha$) and correct the sum of the thermal currents which have occurred, to zero, allowing for a residual error ($P_{restmax}$) which results from a permissible contouring error ($\theta_B$, $\theta_B$). The release of heat from the mixing propeller (Q) is used to obtain a rapid compensation. In addition, a number of improvements have been made to the construction of a device for carrying out the inventive method. Overall, said inventive method results in much more accurate measurement results. The method and device can be used in all fields in which the determination of the salt content of liquids is of interest, for example, in oceanography and in this particular field, in polar research.

19 Claims, 3 Drawing Sheets

U.S. PATENT DOCUMENTS

| | | | | |
|---|---|---|---|---|
| 3,878,456 | A | * | 4/1975 | Stephan et al. ............... 324/448 |
| 3,906,354 | A | * | 9/1975 | Murdock .................... 324/448 |
| 3,963,979 | A | * | 6/1976 | Dauphinee ................. 324/444 |
| 4,511,845 | A | * | 4/1985 | Dauphinee et al. .......... 324/444 |
| 4,652,811 | A | * | 3/1987 | Kwiat et al. ................ 324/696 |
| 4,672,322 | A | | 6/1987 | Gratteau et al. ............. 324/441 |
| 5,025,222 | A | * | 6/1991 | Scott et al. .................. 324/639 |
| 5,739,420 | A | * | 4/1998 | Peterson ................. 73/40.5 R |
| 6,404,204 | B1 | * | 6/2002 | Farruggia et al. ........... 324/441 |
| 2002/0135377 | A1 | * | 9/2002 | Farruggia et al. ........... 324/441 |

OTHER PUBLICATIONS

Fracassi da Silva, J.A. et al.: "Development of a Digital Conductivity Meter with Frequency Response for Remote Monitoring"; Instrumentation Science & Technology, 26(4), pp. 409-420; (1998).

Bianchi, H. et al: "A cell for the study of the electrolytic conductivity at high temperature in aqueous solutions"; Rev. Sci. Instrum. 64 (4), Jun. 1993; pp. 1636-1640; New York.

* cited by examiner

(invention: LRM)

METHOD FOR DETERMINING THE SALT CONTENT OF LIQUID AND DEVICE FOR CARRYING OUT SAID METHOD

BACKGROUND OF THE INVENTION

Field of the Invention

The invention relates to a method of determining the salinity of liquids by standard calibrated measurements of the electrical conductivity of a liquid sample of predetermined temperature in a measuring cell arranged within a cooled and mechanically stirred as well as heatable water bath which is insulated to the outside, under controlled parametric consideration of the thermal conditions in the water bath, and to a device for practicing the method.

State parameters in a thermodynamic sense unequivocally define the state of a liquid. Taking sea water in particular as a well-defined liquid, three state parameters, also known as thermodynamic functions, are sufficient for the definition; all other parameters may be derived therefrom. The thermodynamic functions of temperature, salinity and pressure are considered by classical oceanography to constitute the simplest and most precisely measurable state parameters. Since about 1960 it has been possible by using electrical sensors continuously to measure in situ electrical conductivity, temperature and pressure of the sea. Instead of the classical parameter "salinity", "electrical conductivity" is included in the set of the three measured characteristic values defining the state of sea water, because it can be measured more easily in situ and may be converted into salinity by means of an empirical normalized formula. Therefore, even though nowadays the salinity would no longer be required to define the fluid density, one would have to have recourse to it to understand oceanic processes. As a conservative value, the salinity remains constant at changes in temperature and pressure, and it is also not affected by the metabolism of plants and animals living in the sea. It is subject to simple rules resulting from the preservation of the water and salt masses, when sea water of different salinities is mixed. For that reason, the salinity is ideally suited for characterizing bodies of water and as a tracer for examining large volume currents. But the knowledge of given salinity may also be important in other fluids, such as, for instance, pharmaceutical chemistry or food analyses.

Various methods and apparatus for defining the salinity of fluids are known in the prior art. Japanese patent JP 63111457 (1988) discloses a method by which the salinity is determined on the basis of the parameters of temperature, pressure and speed of sound. To this end, ultra-sonic measuring paths are positioned in a submarine area for recording the time lag between transmitter and receiver of oscillator-generated sinusoidal ultrasound signals.

Japanese Patent JP 60161554 (1985) discloses another method of carrying out in situ measurements of the salinity of sea water, in which a coil of appropriate winding diameter and length is lowered into the sea in a non-magnetic, non-metallic and waterproof container and is charged with an alternate voltage. The magnetic flux then permeates the surrounding sea water. The conductivity and, hence, the level of the induction current through the water is defined by the salinity. The induction current in the water generates a counter induction in the coil which weakens the current in the coil. The measured coil current is then a direct value of the salinity of the sea water. The indicated method was introduced as early as 1957 in the paper "Gerät zur Schnellregistrierung in der Ozeanographie" (Apparatus for Rapid Registration in Oceanography) by H. Hinkelmann (Z. f. angewandte Physik einschl. Nukleonik, Volume IX, H10, pp. 505-513). The sea water resistance is used as an arm of an almost balanced alternate current bridge. By a complex bridge resistance, a phase angle which depends upon the sea water resistance is generated between the input and output voltages. This phase angle defines the frequency of an oscillator containing the alternate current bridge. The corresponding apparatus to carry out the two methods are laboratory devices for the calibration of in situ devices. More detailed descriptions relating to these apparatus may be found in the papers "A conductivity bridge for measurement of the salinity of sea-water" (1956, Schleicher, Bradshaw, Journal Conseil Permanent International pour l'Exploration de la Mer, Volume 22, pp. 9-20); "A modification of the Werner-Smith-Soule salinity bridge for the determination of salinity in sea water with details of construction, operation and maintenance (Paquette, 1958, Univ. Of Washington, Department of Oceanography, Technical Report No. 54-14, pp. 1-57); "A new automated laboratory salinometer" (1975, Dauphinee, Klein, Sea Technology, Volume 16, pp. 23-25) or "Progress in the measurement of salinity and oxygen at the Woods hole Oceanographic Institution" (1987, Knapp, Stalcup, Technical Report, WHOI-87-4, Woods Hole Oceanographic Institution, pp. 27 seq.).

Japanese Patent JP 62085852 (1987) describes a method of measuring the salinity in liquids the temperature of which differs from a reference temperature. To this end, the measured conductivity voltage is divided by a temperature-dependent compensation voltage. In the apparatus known from the paper "An inductive salinometer" by Brown and Hamon (1961, Deep-Sea-Research, Volume 8, pp. 65-71) the temperature dependence is balanced by NTC (negative temperature coefficient)-thermistors.

A method of determining salinity is known from Canadian Patent CA 1,199,367 or its corresponding U.S. Pat. No. 4,511,845, which is based upon defining a rate of conductivity of sample water relative to standard sea water. The essential contents of these patents has also been published in the prospectus "Laboratory Salinometer—Autosal—Model 8400 A" of Guildline Instruments, Ltd., P.O. Box 99, Smith Falls, Ontario, K7A 4S9, Canada. The invention proceeds from this prospectus as the closest state of the art. Since this is, however, merely an apparatus pamphlet, the basic measurement method which has also been described in the patents will first be described.

The principle of the method of the Autosal (AS) 8400 is that the electrical conductivity of a sea water sample is measured after the form factor of the measuring cell and the sample temperature of sea water has been implicitly defined as normal. This assumes that the form factor and the temperature will remain constant until a following standardization. The ratio of the conductivity of a sample of sea water is defined at a predetermined temperature relative to a sample of standard sea water. The salinity is calculated in accordance with the "Praktische Salzgehaltsskala of 1978" (Practical Salinity Scale of 1978). The temperature term of this formula affects the result of the salinity calculation insignificantly, so that the actual temperature during the measurement need not be known precisely. It is, however, important that the temperature present at standardization remain stable. As the conductivity of sea water is strongly dependent upon temperature every temperature drift fully affects the result. For the intended accuracy of the salinity measurement the temperature between two standardizations must for this reason be kept constant with great accuracy. In order to attain this constancy, which puts great demands on the temperature control and upon the maintenance of ambient conditions, the method of operation for attaining the best possible accuracy should settle over the course of four days at least. The same applies following every disturbance in the operating sequence, for instance, by mistakes in the manual operation. In order for the water of the sample attaining the same temperature as the water bath, the sample is conducted through a metal capillary positioned in the water bath, the capillary functioning as a heat exchanger. Where as a result of too great a difference in temperatures, the heat exchanger is incapable of bringing about full temperature equalization, the second condition is not met. In case of a deviating sample temperature the heat exchanger transmits heat to the bath which may lead to a change in temperature which may exceed permissible tolerances.

Operational experience with the measuring method realized with the AS 8400 has shown that even sample temperature differences permitted by the manufacturer may lead to impermissible temperature changes of the water bath. Any occurring malfunctions cannot be satisfactorily counteracted. In order to take accurate measurements, it is thus necessary to practice the known measuring method in a highly constant climatized room of the kind which for purposes of field tests are available only on few research ships. In the case of ships which have no such complex laboratory equipment the samples must, therefore, be examined in institute (home-based) laboratories. However, during the usual storage times of at least four weeks until the ship returns to its home base, the sample may suffer [from] significant changes. In summary, the known method and the apparatus for practicing it are subject to too great a dependence upon the ambient and operating conditions and upon the operating person.

OBJECTS OF THE INVENTION

The object of the present invention is to avoid the difficulties arising in connection with the known method and, in addition, to provide a markedly improved apparatus for practicing the method by a number of suitable technical measures. Another object of the invention is to provide improved measuring precision by a simple and safe operation. Furthermore, consideration is also to be given to automation and economy.

SUMMARY OF THE INVENTION

In the method in accordance with the invention, the problem is solved by the actual temperature of the water bath being measured with high repetitive precision as an equivalent of the sample temperature, taking into consideration a maximum permissible lag error between the temperature of the water bath and the sample as demanded by the accuracy of the salinity measurement and the control parameters for considering the thermal conditions derivable from the drift in time of the temperature of the water bath, the maximum value of which is defined as the quotient of the maximum permissible lag error and a time constant of the measuring cell for balancing the temperature between the interior of the cell and the water bath.

The method in accordance with the invention avoids the necessity of keeping constant the temperature of the water bath otherwise needed to accommodate the thermal conditions in the water bath, the control of which is extremely difficult primarily because of time lags occurring in the control loop. The temperature of the water bath may now adjust itself in accordance with unadulterated ambient conditions. In case of changes, the rate of change only has to stay within predetermined limits, otherwise a balance control will intervene. For this reason, the method may be practiced in a normal laboratory. The actual water bath temperatures are measured at a high repetitive accuracy, i.e. at a high resolution, and are put in relation, as control parameters, with the registered interval between individual measurements or for purposes of a standard calibration to determine the drift in temperature over time. The standard calibration is based upon the actual values of the actually used standard sea water sample, and allowances are made for possible calibration errors of the temperature sensor. Accordingly, to define the salinity of the liquid sample the indicated temperature of the water bath may be used without further consideration of any measuring error of the temperature sensor.

The basic condition for this approach is the assumption of equivalence between the sample temperature $\theta_{p1}$ relevant to the salinity of the liquid sample liquid and the water bath temperature $\theta_B$ which can be measured without substantial influence. The sample temperature $\theta_{p1}$ cannot, however, be measured with sufficient accuracy in the measuring cell without impermissibly affecting the measurement of the conductivity. In this connection, the term "equivalency" is to connote that the equality between the sample temperature $\theta_P$ and the water bath temperature $\theta_B$ is postulated only up to a permissible difference. This permissible difference is, in fact, a "lag error" $\Delta\theta = \theta_B - \theta_P$ which is caused by the fact that bath and sample do not at once have the same temperature when the bath temperature $\theta_B$ changes. Its maximum permissible value is determined as "maximum permissible lag error" $\Delta\theta_{max}$ as a function of the desired accuracy of the result of the salinity.

In the first CTD measurements the accuracy of the temperature measurement was in the range of 10 mK. However, more precise measurements were made possible as a result of progress in the measuring technique. These became mandatory as oceanographers focussed on polar regions. There, the present range of values is strongly reduced relative to the main ocean, and the range in the vicinity of the freezing point of water in particular is relevant so that a correspondingly higher measurement accuracy in the range of 1 mK should be aimed at. In order to achieve it, improved measurement processes and components immune from cross currents (transverse influences) are required as are reproducible calibration processes and more stable standards. The largest permissible error aimed at nowadays, should be below $10^{-3}$ in the salinity the measurement of which has no unit. This corresponds to a maximum relative error of $3 \cdot 10^{-5}$. To this end the temperature or lag error must be less than 1 mK.

In the method in accordance with the invention the regulation aims at balancing the positive and negative heat currents into the water bath so that its temperature change in time remains less than a predetermined limit value "maximum permissible drift" $\alpha_{max}$. If it is attained or exceeded the measurements will stop. The control of a resulting heat current is simpler than the control of a rigidly determined temperature maintained within narrow limits, and it achieves its goal substantially faster than the latter. The control unit used need now only recognize a temperature drift and, except for a permissible residual error, reduce the sum of the heat currents to zero. A change in ambient conditions now no longer necessitates immediate action by the control which is also important in respect of the measuring frequency and evaluation.

To prove the accuracy of the assumption of equivalence of water bath and sample temperature and for defining limit values and numeric examples for the values set forth supra reference is made to the end of the general description.

An apparatus for practicing the invention is closely connected to the method in accordance with the invention and the principles practiced. In order clearly to set forth these connections, including different embodiments, and the differences relative to the prior art, and in order to prevent repetitions, a preferred apparatus in accordance with the invention for practicing the method in accordance with the invention will initially be explained in greater detail.

The prior art upon which the invention is based for realizing a corresponding measuring apparatus is constituted by the generally acknowledged standard apparatus "Autosal (AS) 8400" referred to supra, of the Guideline company. This is an apparatus in which a liquid of predetermined temperature can be transferred from a sample bottle to a measuring cell arranged in a water bath equipped with a means for cooling, stirring and heating as well as with a heat exchanger, and which at its wall is provided with an exterior insulation, and which is provided with a control unit for adjusting the thermal conditions in the water bath. Further explanations of details of the known apparatus will be given in connection with corresponding embodiments of the invention.

With a view to distinguishing the apparatus in accordance with the invention from the known apparatus, the name "conductivity-reference-measuring-place" (LRM) has been chosen for the former. At the time the AS 8400 was conceived, thermometers with long-time measuring errors smaller than 0.3 mK were exceedingly expensive. For that reason, the known measuring method aimed to maintain a temperature constant rather than to measure it. Modern requirements, however, are no longer satisfied by a constant temperature of the bath; this technology is substantially exhausted whereas the present invention is capable of meeting substantially higher specifications.

The decisive improvement of the method in accordance with the invention is the fact that the temperature is no longer maintained constant; rather, its permissible change is measured taking into account the maximum permissible lag error. Errors of the thermometer used resulting from insufficient calibration or long-term drift are arrested by the standardization, so that the temperature of the water bath is measured directly. In terms of a device for practicing the inventive method, the solution to the problem referred to supra may be seen in a precision thermometer having a long-time drift of less than 1 mK per year and a time constant below 0.5 s. The precision thermometer may be provided with platinum resistors, for instance, and preferably, in a further embodiment of the invention, is provided with temperature immune semiconductor resistors. Such thermometers are extremely robust and insensitive to shock yet highly accurate. The semiconductor resistors are so-called "hot conductors" (NTC thermistors) the resistance values of which decrease with increasing temperatures. A temperature selection dial of the kind provided, for instance, in the known AS 8400 for fine-tuning one of several different temperatures, is not required for the inventive LRM.

In the method according to the invention, the control is realized in a control circuit in which the balanced heat currents constitute the control parameter and a corresponding heat current constitutes the setting parameter. In accordance with an improved embodiment of the inventive method it is advantageous to maintain the maximum permissible value of the drift over time of the water bath temperature by a low-delay and rapid balancing of the heat currents flowing into and out of the water bath such that the resultant value of the heat current does not exceed a predetermined maximum. Control of the residual heat current $P_{ges}$ composed of the heat current components for cooling $P_K$, heating $P_H$, ambience $P_I$, stirring $P_R$, sample $P_P$, measuring $P_M$ and illumination $P_B$ may be easily provided, and deviations may be quickly and simply compensated. Details of individual components have been described at the end of the general description.

In accordance with a further embodiment, in this kind of residual heat control it is reasonable to maintain the bath temperature $\theta_B$ at an approximate deviation of ±1 K at the mean temperature $\theta_L$ by means of the resulting residual heat current $P_{ges}$. This leads to low heat currents because of the insulation of the water bath. The goal is to use the ambient temperature $\theta_L$ as the input for controlling the process sequence. The ambient temperature may occur automatically without complex measures such as, for instance, providing thermostats. All control and adjustment processes are thus based on a sure but simple support.

If it is assumed that the heat current $P_K$ extracted from the water bath by constant cooling is constant and the other heat currents are difficult to affect or negligible, heat balancing in accordance with the invention may in the simplest manner be adjusted by changing the heat current $P_H$ by controlled heating. By means of a mean heat output $P_{hm}$, the sum of the heat currents $P_{ges}$ may be controlled to zero since the permissible temperature drift $\alpha_{max}$ is not exceeded.

In accordance with a further embodiment of the invention it is of particular advantage also to utilize the input of energy into the water bath by stirring for rapid and low-delay controllable heating. To this end, in an advantageous embodiment of the apparatus, the stirrer for stirring and heating the water bath may be a rotation-controllable stirring propeller similar to a ship's propeller of high efficiency which may be [driving] driven by a continuously controllable electric motor arranged outside of the water bath.

Heating of the water bath is carried out by the stirrer by conversion of mechanical energy into thermal energy so that the cooling output $P_K$ must be compensated by the stirring output $P_R$ and the heating output $P_H$ is eliminated as an independent value. It is reasonable to select a cooling output which is equal to the sum of the minimum stirring power necessary to ensure minimum intermixing in the water bath and of the amplitude of the two varying heat currents. Heating of the water bath is accomplished by utilizing the frictional heat of the stirrer which is added proportionally to the water bath. Since heat is generated at the exterior of the stirrer and in the water by internal friction and since the heated water is distributed directly by the stirrer, a greater degree of distribution is now achieved with practically no time delay in view of the fact that there is no longer any heat capacity and no heat resistance of an additional heating element. For this purpose, a good hydrodynamic efficiency of the stirring wing is advantageous.

The ship's propeller used to this end as well as the kinetic energy of the water provide for the rapid and homogenous distribution in the bath of the energy converted to heat at the stirrer. Additional heat input from the heat of the motor is prevented by arranging the electric motor outside of the water bath. Such electric motors, as well as, for instance, electrically commutated direct current motors, are simple and robust. Control of their rotations is accomplished with low lag and quickly. In the known apparatus AS 8400 the constant temperature of the water bath is set at a great time delay by two heat lamps using thick-walled glass cylinders as sources of heat and controlled by two NTC sensors and a dual point control. For that reason, the heat lamps may be viewed as an unfavorable structural element for the control of temperature.

In the known AS 8400 the continuously running cooling of the water bath is performed by a Peltier element provided with an air heat exchanger at the warm side. Such cooling has a relatively low heat resistance and is very sensitive to external temperature changes. For that reason, another embodiment of the method in accordance with the invention provides for [a] high heat resistance of the external insulation. To that end the apparatus in accordance with the invention is advantageously provided with at least one Peltier element in the wall of the water bath which at the cooling side provides for thermal insulation in the water bath. Owing to the high heat resistance the heat current $P_l$ is limited by the exterior skin of the water bath. An analysis of the bath insulation has shown, however, that it is of little use simply to increase the wall thickness of the insulation because of the heat resistance of the insulated wall being positioned in parallel to that of the water bath cooling. The latter is composed of the resistance of the Peltier element which in the usual size has a heat resistance of 1 K/W, and of the resistance of heat exchangers connected in series therewith. At the surrounding side the heat exchanger usually has a very low resistance. Therefore, changes in temperature in the vicinity bring about very strong changes in the heat flow into the bath which may result in impermissible temperature changes. By this way of low heat resistance the effect, therefore, remains largely independent of the remaining insulation of the bath.

In general, the heat exchangers at the side of the bath are connected to a Peltier element with the lowest possible heat resistance in order to achieve as great an effectiveness of the cooling element as possible. In accordance with an advantageous further embodiment of the invention the heat resistance of the water bath cooling at the side of the bath is high in order further to improve the heat resistance of the water bath relative to its environment. Therefore, an insulation is deliberately provided, the reason for it being that a predetermined heat flow over a small heat resistance is obtained by a correspondingly low temperature difference. If the same heat flow is to be obtained over a greater heat resistance which provides improved insulation of the bath from the environment, the temperature difference has to be increased which is to say that the cold side has to be operated at a lower temperature. If the room temperature then changes by a predetermined value, the temperature at the cold side will change by about the same value. But in the case of a high heat resistance the change in the relative temperature difference is less than in the case of a low heat resistance. The heat flow will change correspondingly less, there will be less disturbance of the bath at the same change in temperature of the environment as is the case in the known operation. That, of course, is the aim of the embodiments. An additionally improved external insulation can only augment this effect. However, the useful heat pumping capacity (product of the pumped heat flow and the temperature difference improve above the cooling element) is then reduced by the greater return heat flow. This may be compensated, for instance, by parallel operation of two cooling elements. For improved clarity, a numeric example for explaining these concepts has been set forth at the end of the general description, where relevant values, interconnections and formulae as well as numeric examples have been explained in greater detail.

In the method known from the prior art, the samples and the standard sea water are stored, for raising them to the same bath temperature, in the same room during the input process. In the actual operating process, the samples are adjusted in a heat exchanger in the water bath to the temperature of the bath. At common temperature differences between bath and sample this is carried out with adequate accuracy. However, the heat quantity which at deviating temperatures is carried into the bath with the sample must not be ignored. It is in rough field operations where greater temperature differences cannot be avoided. For that reason, it is advantageous in a further embodiment of the method in accordance with the invention to adjust the temperature of the liquid sample to the temperature of the water bath in a separately controlled advance bath. It is also possible quickly and highly precisely to perform measurements of fresh samples in the advance bath without long delays for compensating measures. The large heat exchanger in the water bath is divided, and a portion of it is arranged in a small advance bath the temperature of which may be adjusted to the temperature of the bath with a maximum deviation of ±0.3 K. Samples may then be processed the temperature of which may differ from the temperature of the bath by up to the range of 4 K. When exiting from this advance bath the sample will have discharged almost its entire excess energy, and in the second portion of the heat exchanger in the water bath, it will be adjusted precisely to the temperature of the bath without any significant flow of energy. The demands on the control may be easily satisfied. The advance bath is provided with a cooling element of low heat resistance as it need not be especially well insulated from the environment. At the required low precision of control and the low required efficiency the cooling element may also be used for heating by flow reversal.

In order further to improve the known method a further embodiment of the invention provides for an automatic and computer-controlled measuring operation and for calculating the salinity of the liquid sample on the basis of the measured values for temperature and conductivity in accordance with the UNESCO formula. As a result, the chronological measuring operation is more substantially and more uniformly determined by the apparatus which improves the quality of the measurements. Errors in the operation of the apparatus and in the operating sequence may be substantially avoided. The reproducibility of the results of the measurements is improved. It is possible more economically to utilize the required apparatus in a permanent operation as monitoring and operating requires attention at lower levels of concentration.

An important value in connection with the heat flow balance of the water bath is the heat input by the sample itself. With the known AS 8400, there is no advance heating, and the volume of the measuring cell is about 15 ml. Continuous sequences of measurements with continually new fillings of the measuring cell lead to corresponding disturbances of the temperature of the water bath and, hence, to extended balancing times. For that reason, it is better to provide a measuring cell of a volume of about 2 ml and strip electrodes, as is the case in a further embodiment of the apparatus in accordance with the invention. Such a small volume, because of the small ratio of its volume relative to the water bath allows for a greater difference in temperature relative thereto. This means a further simplification of the pre-heating of the sample and an improved processing rate. Instead of the conventional glass side ducts for accommodating the electrodes in the measuring cell the apparatus in accordance with the invention utilizes simple strip electrodes affixed by and baked in by a platinum paste.

The possibility of preheating the sample in accordance with the invention may be realized, according to a further embodiment of the invention, by providing a separate controllable advance bath provided with a heat exchanger for heating the liquid sample. Such an advance bath, having a volume, for instance, of 0.5 l is of very simple construction and may be integrated into the LRM without any difficulties. Cooling is provided in a known fashion by a Peltier element in particular. Heating may be accomplished by the cooling element by flow reversal thus making use of the heat exchanger for cooling as well as for heating.

At the beginning and at the end of the measuring sequence, but at least twice daily, the known AS 8400 is standardized. For this purpose a vial of standard sea water is shaken, opened and connected to the sample suction hose. The measuring cell is then filled by means of a peristaltik pump. The measuring cell may be observed through a window in order to prevent interfering air bubbles and to shut down the pump before the sample water reaches and plugs up the vent capillaries. For emptying the measuring cell an air hole in the front plate through which pressurized air escapes from the measuring cell is stopped by a finger of an operator. This leads to the generation of higher air pressure over the sample water in the measuring cell for pressing the sample water out of the cell by way of a siphon, thus emptying the measuring cell. The peristaltic pump still remains filled with sea water, however. This filling and emptying is repeated several times.

According to a further embodiment, the LRM is provided, for carrying out standard calibrations and measurements, with a four-way valve having channels leading to a vial of standard sea water, to a bottle of sample water as well as to a cleaning and air channel. Such a four-way valve allows simple selection between connected media. The measuring cell is evacuated by way of a capillary protected from plugging up; the cell may be automatically filled by simple actuation of the four-way valve. For evacuating the sample liquid following a measurement, it is advantageous in accordance with a further embodiment to provide a diaphragm pump. This diaphragm, pump which may be of small dimensions, will generate pressurized air only when the cell vent is connected to the diaphragm pump by way of a simple two-way valve. By separating the air currents, pressurized air need be generated only when it is needed. When changing samples during rinsing, the entire system, including the pump, is evacuated; the sample water is thus more thoroughly changed and measurement errors are reduced.

Heretofore, the use of a peristaltic pump has required visual inspection of the filling state of the measuring cell. The ability completely to fill the measuring cell automatically is an important step toward automation of the measurements. For that reason it is advantageous to provide, as proposed by a further embodiment of the invention, a dosage pump which requires no observation while the measuring cell is being filled. This may be a peristaltic pump in view of the fact that with the LRM venting is no longer as sensitive as it is with the known AS 8400; the measuring cell is no longer damaged if it is slightly overfilled. The use of an optical level sensor is also possible.

Several measures may be realized in connection with the LRM in accordance with the invention to bring about further improvements, such as, in particular, providing a personal computer for regulating the water bath, for controlling the measuring sequence and for storing the results of measurements; conducting the measurement of the conductivity of the sample liquid with a fully automatic precision balancing bridge; and providing an indicator to show satisfaction of the measuring conditions. In the known AS 8400 the setting, balancing and standardizing operations are performed manually by appropriate devices, buttons and potentiometers. No potentiometers are provided in the LRM. The so-called $K_{15}$-value of the standard sea water vial is input only once, and three sufficiently conforming measurements are taken of the conductivity of the standard sea water. The $K_{15}$-value connotes the conductivity ratio at 15° C. and normal pressure of a predetermined solution of potassium chloride the concentration of which is set such that its conductivity is the same as that of standard sea water at 15° C. Bridge balancing is accomplished automatically at all positions. The salinity is calculated on the basis of the temperature measured in the water bath, the equivalence with the sample temperature of which is assumed, and the conductivity is measured according to the UNESCO formula. During standardization the form error of the measuring cell and a possible calibration error of the precision thermometer are determined. The time-wise measuring sequence is defined much more by the apparatus and is thus more uniform than is the case with the know apparatus. This improves the quality of the measurements. The standard sea water vial remains in the apparatus, the sample hose is not changed and cannot pollute the standard sea water. An operating state unsuited for taking measurements, such as, for instance, too great a temperature drift in the water bath, is indicated in the LRM by an appropriate display. In general, the LRM may be constructed entirely of components readily available on the market. This is cost-efficient and maintenance-friendly.

EXPLANATIONS OF THE BASES OF THE INVENTION

Numeric Examples

I) Proof of the Assumption of Equivalence Between the Temperatures of the Sample and of the Water Bath The temperature of the water bath changes as $$\frac{dT_B}{dt} = \frac{1}{C_B} P_B \qquad (1)$$

wherein $C_B \rightarrow$ heat capacity $P_B \rightarrow$ resulting heat flow $T_B \rightarrow$ temperature of the water bath The temporal behavior of the temperature of the water bath at constant but not wholly balanced heat flow is $$T_B = \alpha t + T_0 \qquad (2)$$

wherein $$\alpha = \frac{dT_B}{dt} \rightarrow \text{change over time of the bath temperature drift}$$

$T_0 \rightarrow$ temperature of the bath at time $t_0$

It is a precondition of the equivalence calculation the time-wise behavior of the measuring cell and of the thermometer may be represented as a first order differential equation $$T_M = T_M \frac{dT_M}{dt} = \alpha t + T_0 \qquad (3)$$

wherein $\tau_M = R_T \cdot C_T \rightarrow$ time constant of the thermometer $T_M \rightarrow$ measured temperature $R_T \rightarrow$ thermal resistance water bath—thermometer $C_T \rightarrow$ heat capacity of the thermometer The differential equation, by adding a term for the calibration error, is solved as $$T_M = T_0 + \alpha t - \alpha T_M \left(1 - e^{-\frac{t}{\tau_M}}\right) + \Delta T_M \quad (4)$$

wherein
$\Delta T_M \rightarrow$ calibration-error
For times $t \gg \tau_M$ equals $T_M = T_B - \alpha t M$
The largest deviation between thermometer and the temperature of the measuring cell is $$T_M - T_{MC} = \alpha(\tau_M - \tau_{MC}) + \Delta T_M \quad (5)$$

wherein
$T_{MC} \rightarrow$ temperature of the measuring cell
$\tau_{MC} \rightarrow$ time constant of the measuring cell
The time-wise course of the difference of the temperatures of the thermometer and measuring cell is $$T_M - T_{MC} = \alpha \left[\tau_M \left(1 - e^{-\frac{t_1}{\tau_{MC}}}\right)\right] + \Delta T_M \quad (6)$$

wherein
$t_1 \rightarrow$ measuring time 1
The expression between brackets is always between 0 and 1.
The increase in water temperature be assumed to be at just $$\alpha_{max} = = \frac{\alpha}{1 - e^{-\frac{t_1}{\tau_M}}}$$

with a denominator always $\leq 1$ results in $\alpha_{max} \leq \alpha$
and substituted in (6)

$$T_M - T_{MC} = \alpha_{max}\left[\tau_M - \tau_{MC} \frac{1 - e^{-\frac{t_1}{\tau_{MC}}}}{1 - e^{-\frac{t_1}{\tau_M}}}\right] + \Delta T_M$$

Since the time constant of the measuring cell is greater than that of the thermometer by a factor of about 100, with $\tau_{MC} > \tau_M$ the denominator of the fraction is always smaller than the numerator so that the temperature difference always remains below the highest permissible limit from (5). The equivalence precondition of the temperatures between sample and water bath has thus been demonstrated.

In the example, the temperature of the water bath increased more quickly than stated by $\alpha_{max}$, but the indication of the quicker thermometer initially does not exceed this limit value and the measurement by the slower measuring cell will, therefore, not be disturbed. Only if this condition lasts for an extended period, the thermometer and, in the end, the measuring cell as well will reveal an impermissible temperature increase. Upon reversal of the drift conditions it will, of course, be necessary, following indication of permissible conditions by the thermometer, to wait for a definable time until measuring conditions of the measuring cell have also been restored. In automatic measurements, the controlling computer will detect the maintenance of the measuring conditions.

II) Lag Error, Temperature Drift

An increase in the temperature $\theta_B$ of the water bath under the influence of temporally constant set value always follows a linear time path (analogously to capacitive control circuits with set values of current and voltage). The time constant of the measuring sensor (0.1 s) usually is very small and may be ignored by comparison with a time constant $\tau$ of the measuring cell, which in the AS 8400 is in the range of 28 s, even if a measured value is recorded, for instance, at intervals of 2 s only. The time constant $\tau$ denotes the product of heat resistance of the glass body of the measuring cell and the heat capacity of the filled-in sample. As time lag it is measure of the longest permissible time interval between filling of the measuring cell and the first temperature measurement and constitutes a characteristic of the filled measuring cell and is experimentally defined during manufacture of the apparatus.

The lag error may be calculated from $$\Delta\theta = (d\theta_B/dt) \cdot \tau$$

From this, the temperature drift may be derived as $$\alpha = d\theta_B/dt = \Delta\theta/\tau$$

If, given the preconditions set forth supra, a maximum permissible lag error of the measuring cell is postulated as $\Delta\theta_{max} = 0.3$ mK at a time constant of $\tau = 28$ s, a maximum permissible drift $\alpha_{max} = \Delta\theta_{max}/\tau = 10$ μK/s may be derived from the second equation. This is a quantity statement which is valid for both positive and negative temperature changes. A maximum permissible temperature drift $\alpha_{max}$ of 10 μK/s of the water bath temperature $\theta_B$ may be considered tolerable given the exemplary preconditions and does not lead to a controlled balancing. If the temperature drift $\alpha$ is only of short duration, the lag error would, of course, be smaller than 0.3 mK. At an exemplary maximum permissible lag error $\Delta\theta_{max}$ of 0.1 mK and a time constant of 15 s the resultant value for a maximum permissible temperature drift $\alpha_{max}$ would be about 7 μK/S.

After a time $t_v$ following charging of the measuring cell with a sample liquid preheated for temperature equalization, the conductivity of the sample is measured. If during this time the temperature $\theta_B$ of the bath has increased by the maximum permissible drift $\alpha_{max}$, there will be a lag error $$\Delta\theta_v = \alpha_{max} \cdot T_v$$

between the bath and sample temperatures at the measuring time.

Hence, in pursuit of the first mentioned numeric example a maximum time interval $T_{vmax} = \Delta\theta_{max}/\alpha_{max}$ of 30 s will result between filling and measuring. This time can easily be adhered to. The error generated by this time lag is not added to the actual lag error; but it ought to be set to be smaller than the maximum permissible lag error.

III) Heat Currents

The heat current flowing in and out of the water bath are, in particular, the heat current PK pumped from the water bath by cooling;

the heat current $P_H$ pumped into the water bath by heating;

the heat current $P_I$ generated by the difference in temperature $P_I = (\theta_B - \theta_L)/R_{WI}$ between the environment and the water bath and applied by the heat resistance of the water bath insulation;

the heat current $P_R$ input into the water bath by stirring;

the heat current $P_P$ input into the water bath by the sample which may be continually newly filled into the bath, if its temperature is different from the temperature of the water bath ($P_P = C_W \cdot V/t(\theta_P - \theta_B)$) (V/t=mean volume current during filling);

the heat current $P_M$ input into the water bath by the electrical energy of the measuring sensor; and the heat current $P_S$ input into the water bath by the illumination. It may generally be ignored.

A cover on top of the bath prevents the occurrence of heat currents from evaporation or condensation of room air humidity which would have additionally to be considered. The cooling power $P_K$ is assumed to be constant at a constant flow through the cooling element even though its heat pumping ability depends somewhat from the temperature difference between the warm and the cold side. The heat current through the insulation of the bath container $P_I$ is proportional to the temperature difference between its interior and the vicinity and thus amounts to one of the variable parameters, like the heat, which are input into the bath by samples of different temperature. They develop into a pulsating heat current by the uniform renewed filling of the measuring cell at the mean volume flow V/t. The temperature of the electrical power entering the bath as a result of the measuring sensors may be ignored.

Analogously to Ohm's law a heat resistance law describes the temperature difference $\Delta\theta$ over a heat resistor $R_T$ through which a heat current is flowing as $$\Delta\theta = R_T \cdot P_W$$

If a heat current $P_W$ is flowing in a body of heat capacity $C_W$ the temperature $\theta$ thereof will change as $$d\theta/dt = P_W/C_W$$

The sum of the mentioned heat currents thus changes the temperature of the water bath to $$d\theta_B/dt = 1/C_W(P_K + P_H + P_I + P_R + P_P + P_M)$$

IV) Heat Resistance

The heat resistance of a Peltier element measuring 40 mm×40 mm does not exceed 1 K/W. If the resistance of the insulation of the wall be 1.5 K/W, the total resistance thus is in the range of 0.6 K/W and can be increased to 1 K/W only regardless of the quality of the insulation of the wall. By contrast, the insulation of the Peltier element by a plate of PVC 3 mm thick and measuring 40 mm×40 mm on the side of the bath, will raise its heat resistance to 7 K/W. The side facing the room will, however, be maintained at room temperature by a large cooling body and an intensive ventilator. The total heat resistance will then amount to 1.2 K/W. The additional insulation of the Peltier element will limited, however, the heat current pumped out of the bath to about 5 W because the temperature difference above the insulation plate amounts to 6 K/W·5 W=30 K. If the temperature in the bath is 20° C. the cold side of the Peltier element will be at −10° C. whereas its warm side, because of the heat resistance of the cooling body, will be at about 25° C. In order to be able to pump a heat current of 5 W at a temperature difference of 35 K parallel operation of two or more Peltier elements may be required.

DESCRIPTION OF THE SEVERAL DRAWINGS

The novel features which are considered to be characteristic of the invention are set forth with particularity in the appended claims. The invention itself, however, in respect of its structure, construction and lay-out as well as manufacturing techniques, together with other objects and advantages thereof, will be best understood from the following description of preferred embodiments when read in connection with the appended drawings, in which:

DETAILED DESCRIPTION OF THE PREFERRED EMBODIMENTS

Figure 1:
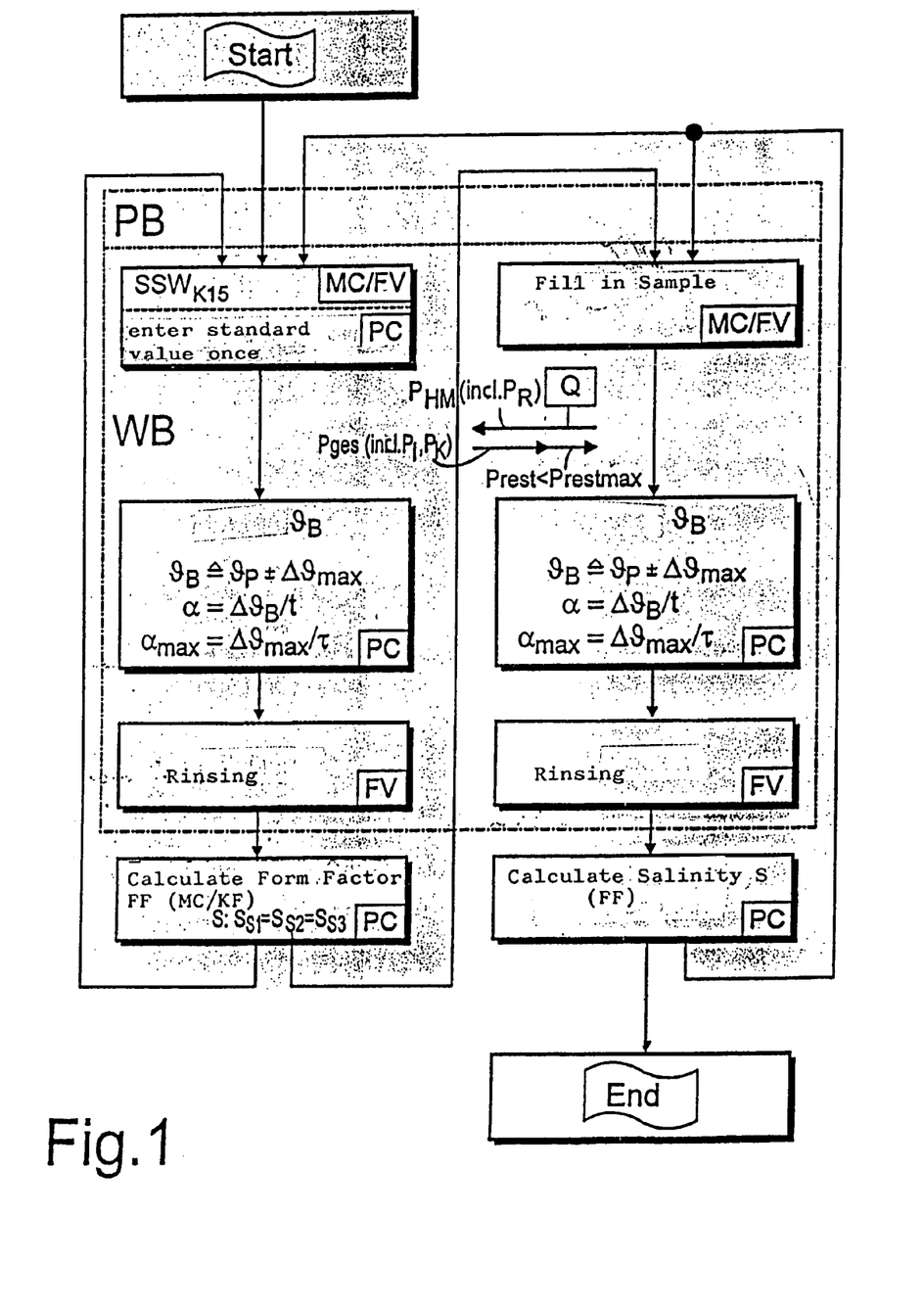
FIG. 1 depicts a flow diagram of the method in accordance with the invention.

FIG. 1 depicts the steps typical of the method in accordance with the invention as a flow diagram. Initially a standard calibration is performed with standard sea water SSW by the $K_{15}$-value. In its sequence the calibration flow corresponds to the measuring flow described infra. If the results of three salinity measurements are $S_{s1} = S_{s2} = S_{s3}$ the calibration will have been successfully concluded. Balancing of the bridge occurs automatically. A status report and the result are input into a PC. The form factor FF of the measuring cell MC and a possible calibration error KF of a utilized thermometer will be implicitly taken into consideration during calibration. As long as these measurement errors are small there compilation in a form factor is permissible.

In the ensuing measurement flow a sample PROBE is initially fed through a heatable and coolable advance bath PB to adjust the temperature $\theta_P$ to the temperature $\theta_B$ of the bath. Thereafter, it is conducted into a measuring cell MC arranged in a larger water bath WB. In the measuring cell MC the electrical conductivity κ is measured, and the value is input in the computer PC. Thereafter, the measuring cell MC is evacuated by pressurized air, cleaned by distilled water and filled with a new sample PROBE. The distribution of the flow of the individual media flows is carried out by a four-way valve FV controlled by the computer PC. The measuring flow may be continually repeated. New calibrations are periodically interjected at predetermined intervals.

During measurement of the electrical conductivity κ the temperature $\theta_B$ of the bath is continually measured, and the computer PC, with consideration of the time t between two measurements, calculates a temperature drift α on the basis thereof. In this connection it is assumed that the temperature $\theta_B$ of the bath is substantially identical, except for an arbitrarily determined small lag error $\Delta\theta$, to the temperature $\theta_P$ of the sample in the measuring cell MC. The size of the temperature drift α must be below a predetermined permissible maximum value $\alpha_{max}$ to prevent the occurrence of a control compensation (Regelausgleich). Shortly before reaching the permissible maximum value $\alpha_{max}$ of the temperature drift a mean heat current $P_{Hm}$ (including the kinetic stirring power $P_R$) is automatically altered to a residual heat current $P_{rest}$ by a stirring propeller Q for balancing the entire heat currents $P_{ges}$ including the heat current from the vicinity $P_I$ and a cooling power $P_K$. The residual heat current $P_{rest}$ must not exceed a predetermined maximum residual heat current $P_{restmax}$. Otherwise the control will intervene.

Thus, the control parameter is constituted by the temperature drift α which is set in relation to the maximum permissible temperature drift $\alpha_{max}$. The maximum permissible temperature drift $\alpha_{max}$ is calculated as quotient from the predetermined maximum permissible lag error $\Delta\theta_{max}$ between the bath and sample temperatures $\theta_B$, $\theta_P$ and the time constants $\tau$ ($\alpha_{max}=\Delta\theta_{max}/\tau$). The control value in the control circuit is the heating power $P_H$ input into the water bath WB by the stirring propeller Q, and the disturbance value is the sum of all occurring heat currents $P_{ges}$.

The salinity S of the sample PROBE is finally calculated on the basis of the measured values of the temperature $\theta_B$ of the water bath WB and of the conductivity κ of the filled sample PROBE by a calculation program used in oceanography on the basis of the UNESCO formula. The calculated value and the disturbances in the process sequence are rendered optically visual.

Figure 2:
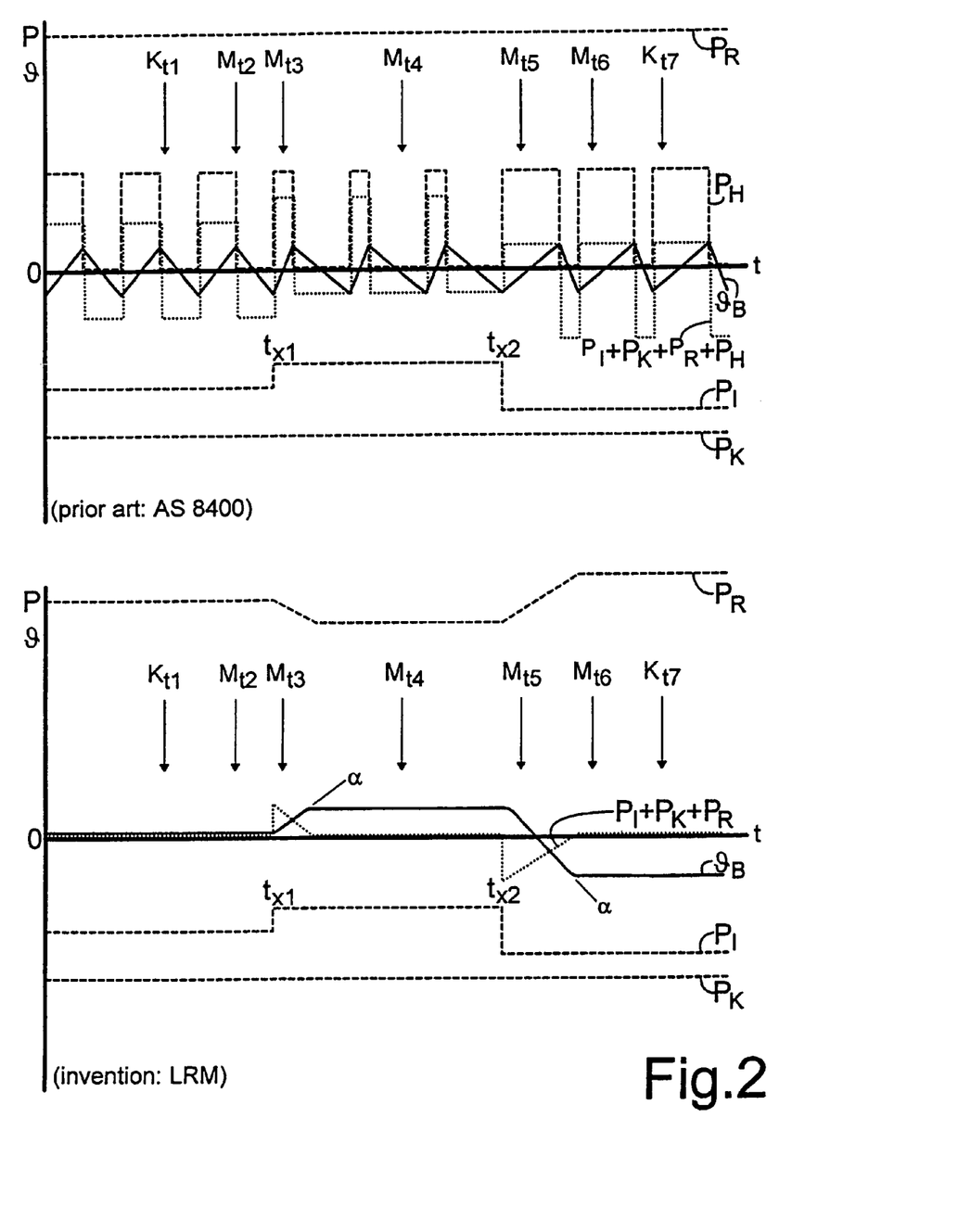
FIG. 2 depicts an energy diagram for balancing a disturbance by the control parameter here termed "temperature drift" and for comparison with the known parameter "temperature"

From FIG. 2 depicts an energy diagram related to given control operations. In order to show an optimum energy balance (at the bottom of the Figure) by practicing the method according to the invention with the LRM, the energy balance of the known method practiced with the AS 8400 is also depicted (at the top of the Figure) for reasons of comparison. The heat currents into the water bath and the heat currents out of the water bath have been depicted as surfaces up to a limit curve, above a time line t. At points in time $t_{x1}$ and $t_{x2}$ abrupt significant disturbances occur as a result of heat currents $P_I$ from the vicinity and which require controlled compensation. For instance, at time $t_{x1}$ a person being a heat source may approach the water bath, at point $t_{x2}$ a door may be opened and heat may escape from the room. In both control methods the cooling power is always constant. In the AS 8400 the stirring power $P_R$ is also constant, and additional heating energy $P_H$ occurs. It is generated by digitally controlled heat lamps. In the LRM the disturbance is compensated by the heating power $P_H$ being augmented by the stirring power $P_R$ as a result of controlling the rotations of the stirring propeller Q. The sawtooth curve of the temperature $\theta_B$ of the water bath may be clearly seen with the AS 8400, the curve being intended to maintain as a control parameter a constant temperature $\theta_B$ of the water bath. By contrast, the temperature $\theta_B$ of the water bath of the LRM depicts a substantially continuous curve. As long as the temperature drift α does not exceed its permissible maximum value further adjustment of the stirring power $P_R$ is not necessary. The known complex maintenance of a constant bath temperate $\theta_B$ has become unnecessary with the :RM. At the depicted point in time for calibrations $K_{t1}$, $K_{t7}$ and measurements $M_{t2}$ ... $M_{t6}$ it can be clearly seen how much the water bath and sample temperatures $\theta_B$, $\theta_P$ may deviate in the prior art from the implicitly assumed temperature, whereas in the method according to the invention it is measured each time except for the maximum permissible lag error $\Delta\theta_{max}$ and is integrated into the calculation of the salinity S. The much greater accuracy of the measurements yielded thereby is obvious.

Figure 3:
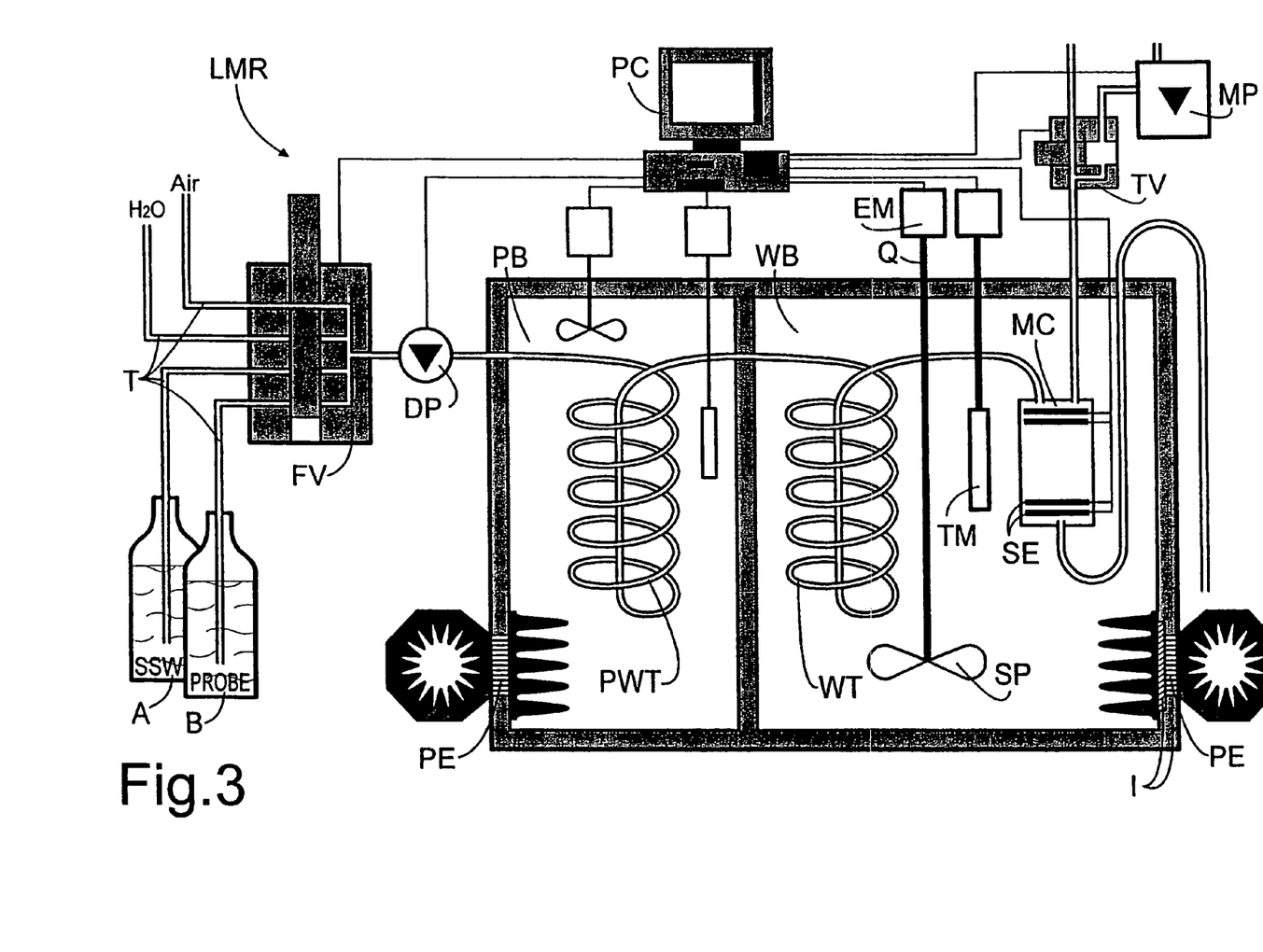
FIG. 3 depicts a block diagram of an apparatus for practicing the method in accordance with the invention.

FIG. 3 depicts a conductivity-reference-measuring site LRM as a preferred arrangement for practicing the method according to the invention. The LRM is provided with a water bath WB and a separate advance bath PB. In the advance bath PB which may be heated as well as cooled by a Peltier element there is provided a preheat exchanger PWT for temperature adjustment between a sample PROBE taken from a sample bottle B (or standard sea water SSW from a vial A for calibration) and the water bath WB. In the water bath WB a measuring cell MC is positioned behind a main heat exchanger WT. The measuring cell is provided with four strip electrodes SE for measuring the changing values of current and voltage. Almost all media flows are fed by a dosage pump DP and flow through hoses T by way of a four-way valve FV acting as a distributor. Pressurized air required for evacuating the measuring cell MC is generated by a diaphragm pump MP as needed and is fed into the measuring cell MC by way of a two-way valve TV. The electrical conductivity κ is measured in the measuring cell MC at a fully automatically balancing precision bridge (not shown) by means of a computer PC. Furthermore, there are provided in the water bath WB a precision thermometer TM for measuring the temperature $\theta_B$ of the water bath and a rotation-controlled stirring propeller Q with a propeller SP similar to a ship's screw for controlling the temperature drift α by way of the mean input heating power $P_{hm}$. In the embodiment shown, it is the commercially available thermometer "SBE3plus" of the "Seabird" company, which because of its stability drifts less than 1 mK during the course of a year and which satisfied the requirements without any problems. The stirring propeller Q is provided with an electric motor EM arranged outside of the water bath and counteracts a continually cooling Peltier element PE which for increasing its heat resistance R is provided with an insulation I similar to the water bath WB.

In the selected embodiment the stirring propeller Q has an operating range between 3 W and 5 W and, hence, a working point at 4 W. Considering the relationship between temperature and heat current ($d\theta/dt=P/C_W$) and the predetermined limit and material values the heat current balance may be balanced with ±1 W. If 0.5 W is reserved for the heat current of the ambient temperature $\theta_L$ may now deviate from the water bath temperature $\theta_B$ by 1 K without the temperature drift α taking on impermissibly high values. At these values, the total resulting heat resistance is 2 K/W. If the resistance of the insulation I of Peltier element PE and heat exchanger WT is 7 K/W the insulation of the bath must be 2.8 K/W. To this end the resistance value may, if necessary, have to be increased.

From the relationship mentioned supra it is possible with the maximum permissible temperature drift $\alpha_{max}=d\theta/dt$ as default and knowing the resulting heat capacity $C_{WB}$ of the water bath WB ($V_W \cdot C_{WS}$) to calculate the tolerable residual error of the heat current $P_{rest}$ to be balanced. For instance, $\alpha_{max}=7$ μK/s and $C_{WB}=67 \cdot 10^3$ Ws/K for a water bath of a volume $V_W=16$ l and a specific $C_{WS}$ value for water of $4.2 \cdot 10^3$ Ws/(1K) result in a power of $P_{rest}=0.47$ W. At an improved heat resistance $R_{WT}=1.2$ K/W of the water bath according to the equation $\Delta\theta=R \cdot P$ the ambient temperature $\theta_L$ may now deviate from the bath temperature $\theta_B$ by 0.56 K without the control having to intervene.

The invention claimed is:

1. A method of determining the salinity of liquids by standard calibrated measurements of the electrical conductivity of a heated liquid sample in a measuring cell, comprising the steps of:
  providing the measuring cell in a constantly cooled and mechanically stirred as well as heatable water bath insulated to the exterior under control parametric consideration of the thermal conditions in the water bath;
  measuring with a thermometer the actual temperature ($\theta_B$) as an equivalent of the temperature ($\theta_P$) of the sample at a high repetitive accuracy and with a maximum permissible lag error ($\Delta\theta_{max}$) between the temperature of the water bath and sample temperature ($\theta_B$, $\theta_P$) set by the required accuracy of determining the salinity (S), a control parameter for taking into account the thermal conditions being the time-wise drift ($\alpha=\Delta\theta_B/t$) of the temperature ($\theta_B$) derivable from the temperature measurements, the permissible maximum value ($\alpha_{max}$) of which is defined as the quotient ($\alpha_{max}=\Delta\theta_{max}/\tau$) of the maximum permissible lag error ($\Delta\theta_{max}$) and a time constant (τ) of the measuring cell (MC) for a temperature equalization between the interior of the measuring cell and the water bath (WB), and controlling with a control device the permissible maximum value of the time-wise drift ($\alpha_{max}$) of the temperature ($\theta_B$) of the water bath by maintaining a low-lag and quickly controllable compensation of the heat currents (P±) flowing into and out of the water bath (WB) such that the resulting quantity of the residual heat current ($P_{rest}$) does not exceed a predetermined maximum value ($P_{restmax}$).

2. The method of claim 1, further comprising the step of maintaining the temperature ($\theta_B$) of the water bath by the resultant residual heat current ($P_{rest}$) at the mean ambient temperature approximately with a deviation of ±1 K.

3. The method of claim 2, further comprising the step of utilizing the energy input into the water bath (WB) by the stirring ($P_R$) for the quick and low-lag controllable heating ($P_H$) thereof.

4. The method of claim 3, further comprising the step of providing high heat resistance (R) of the exterior insulation (I) of the water bath (WB).

5. The method of claim 4, further comprising the step of providing water bath cooling (PE) of high heat resistance (R) on the side of the bath.

6. The method of claim 5, further comprising the step of adjusting the temperature of the liquid sample ($\theta_P$) to the temperature ($\theta_B$) of the water bath in a separately controlled advance bath (PB).

7. The method of claim 6, further comprising the steps of carrying out the measuring sequence automatically by a computer (PC) and of calculating the salinity (S) of the liquid sample (PROBE) from the measured values of temperature ($\theta_B$) and conductivity ($\kappa$) on the basis of the UNESCO formula.

8. An apparatus for determining the salinity of liquids by standard calibrated measurements of the electrical conductivity of a heated liquid sample, comprising:

a vial for holding a sample of the heated liquid;

a measuring cell arranged in a water bath;

means for transferring the heated liquid from the vial to the measuring cell;

means in the water bath for cooling, stirring and heating;

a heat exchanger;

insulation means disposed at an external wall of the water bath;

a control device for controlling the actual temperature ($\theta_b$) of the water bath at high repetitive accuracy and at a maximum permissible lag error ($\Delta\theta_{max}$) between the water bath and sample temperature ($\theta_b$, $\theta_p$) determined by the accuracy demanded by the determination of salinity (S) as the equivalent of the temperature ($\theta_p$) of the sample, the control parameter for taking into account the thermal conditions being the time-wise drift ($\alpha=\theta_B/t$) of the temperature ($\theta_b$) of the water bath the permissible maximum value ($\alpha_{max}$) of which is defined as the quotient ($\alpha=\Delta\theta_{max}/\tau$) of the maximum permissible lag error ($\Delta\theta_{max}$) and a time constant ($\tau$) of the measuring cell (MC) for a temperature balancing between the interior of the measuring cell and the water bath (WB), and means for low-lag and quick adjustment of heat currents (P±) flowing into and out of the water bath (WB) for maintaining a permissible maximum value of the time-wise drift ($\alpha_{max}$) of the temperature ($\theta_b$) of the water bath such that the quantity of the resulting residual heat current ($P_{rest}$) does not exceed a corresponding predetermined maximum value ($P_{restmax}$), and a precision thermometer (TM) having a long term stability of less than 1 K per year and a time constant of less than 0.5 s for directly measuring the actual temperature ($\Delta\theta_B$) of the water bath (WB).

9. The apparatus of claim 8, wherein the precision thermometer (TM) is provided with temperature dependent semiconductor resistors.

10. The apparatus of claim 9, wherein the means for stirring provided for stirring and heating the water bath (WB) is structured as a rotationally controllable stirring propeller (Q) having a stirring vane (SP) similar to a ship's screw of high hydrodynamic efficiency which and is rotatable by a continuously controllable electric motor (EM) arranged at the exterior of the water bath (WB).

11. The apparatus of claim 10, wherein at least one Peltier element provided with a thermal insulation (I) at the cooling side of the water bath (WB) is arranged at the wall of the water bath (WB).

12. The apparatus of claim 11, wherein the measuring cell (MC) is provided with strip electrodes (SE) and has a volume in the range of 2 ml.

13. The apparatus of claim 12, wherein a separate controllable advance bath (PB) with a preheat exchanger (PWT) is provided for heating the liquid sample (PROBE).

14. The apparatus of claim 13, wherein for carrying out standard calibrations and measurements there a four-way valve (FV) is provided which comprises inputs respectively connected to a vial (A) of standard sea water (SSW), a bottle (B) of sample water (PROBE) and to cleaning and air conduits ($H_2O$, Air).

15. The apparatus of claim 14, wherein a diaphragm pump (MP) is provided for evacuating the measuring cell (MC).

16. The apparatus of claim 15, wherein a dosage pump (DP) is provided for filling the measuring cell (MC).

17. The apparatus of claim 16, further comprising a' computer (PC) for regulating the water bath, controlling the measuring sequence, and storing results.

18. The apparatus of claim 17, further comprising a fully automatic precision balancing bridge for measuring the conductivity of the liquid sample (PROBE).

19. The apparatus of claim 18, further comprising an indicator for signaling satisfied measuring conditions.

* * * * *